United States Patent [19]

Lockridge et al.

[11] Patent Number: 5,575,768
[45] Date of Patent: Nov. 19, 1996

[54] DEVICE AND KIT FOR SUPPORTING A BREAST SHIELD AND RELATED PUMP EQUIPMENT

[75] Inventors: Kathleen A. Lockridge, Crystal Lake; Brian H. Silver; Gotthilf Weniger, both of Cary; Richard S. Weston, Crystal Lake, all of Ill.

[73] Assignee: Medela, Inc., McHenry, Ill.

[21] Appl. No.: 555,151

[22] Filed: Nov. 8, 1995

Related U.S. Application Data

[63] Continuation-in-part of Ser. No. 375,977, Jan. 20, 1995, Pat. No. 5,514,166.

[51] Int. Cl.$^6$ .................................................. A61M 1/06
[52] U.S. Cl. .................................................. 604/74; 450/36
[58] Field of Search .................................. 604/74, 75, 73; 128/890; 54/20, 58, 59; 450/36, 37

[56] References Cited

U.S. PATENT DOCUMENTS

| | | |
|---|---|---|
| 22,018 | 11/1858 | Davidson . |
| 22,080 | 11/1858 | Lewis . |
| D. 246,729 | 12/1977 | Murphy . |
| 2,054,491 | 9/1936 | Tynan . |
| 2,436,430 | 2/1948 | Hart . |
| 2,492,862 | 12/1949 | Harvey . |
| 2,495,307 | 1/1950 | Abramson . |
| 2,516,129 | 7/1950 | Leo et al. . |
| 2,585,338 | 2/1952 | Meares . |
| 2,748,771 | 6/1956 | Richards . |
| 2,764,759 | 10/1956 | Gazelle . |
| 3,757,784 | 9/1973 | Avery . |
| 4,270,538 | 6/1981 | Murphy . |
| 4,566,458 | 1/1986 | Weinberg . |
| 4,640,287 | 2/1987 | Anderson et al. . |
| 4,878,879 | 11/1989 | Kunstadter . |
| 5,032,103 | 7/1991 | Larsson . |
| 5,071,403 | 12/1991 | Larsson . |

FOREIGN PATENT DOCUMENTS 1159117  7/1969  United Kingdom .

*Primary Examiner*—Randall L. Green
*Assistant Examiner*—Perry E. Van Over
*Attorney, Agent, or Firm*—Brinks Hofer Gilson & Lione

[57] ABSTRACT

A device is provided for supporting a breast shield of a breast pump upon a woman's breast in a "hands-free" manner. This breast shield support includes a garment that is adapted to a woman's torso, and a mounting element formed with or attachable to the back of the breast shield. Elastic bands tied to loops on the garment are releasably affixed to the mounting element to support the breast shield on the exposed breast. A list for retrofitting the device to a breast pump assembly is advantageously provided.

32 Claims, 5 Drawing Sheets

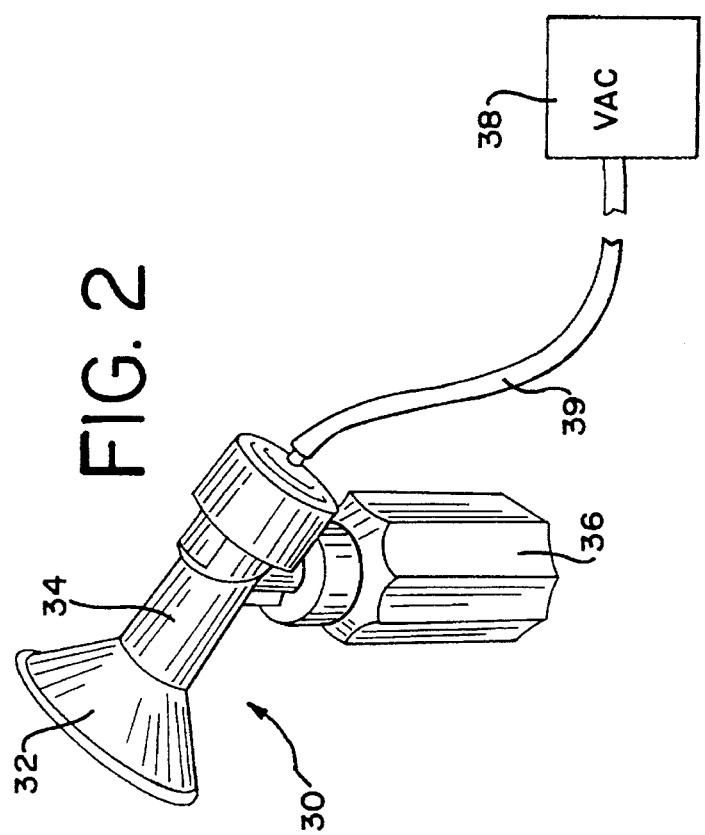
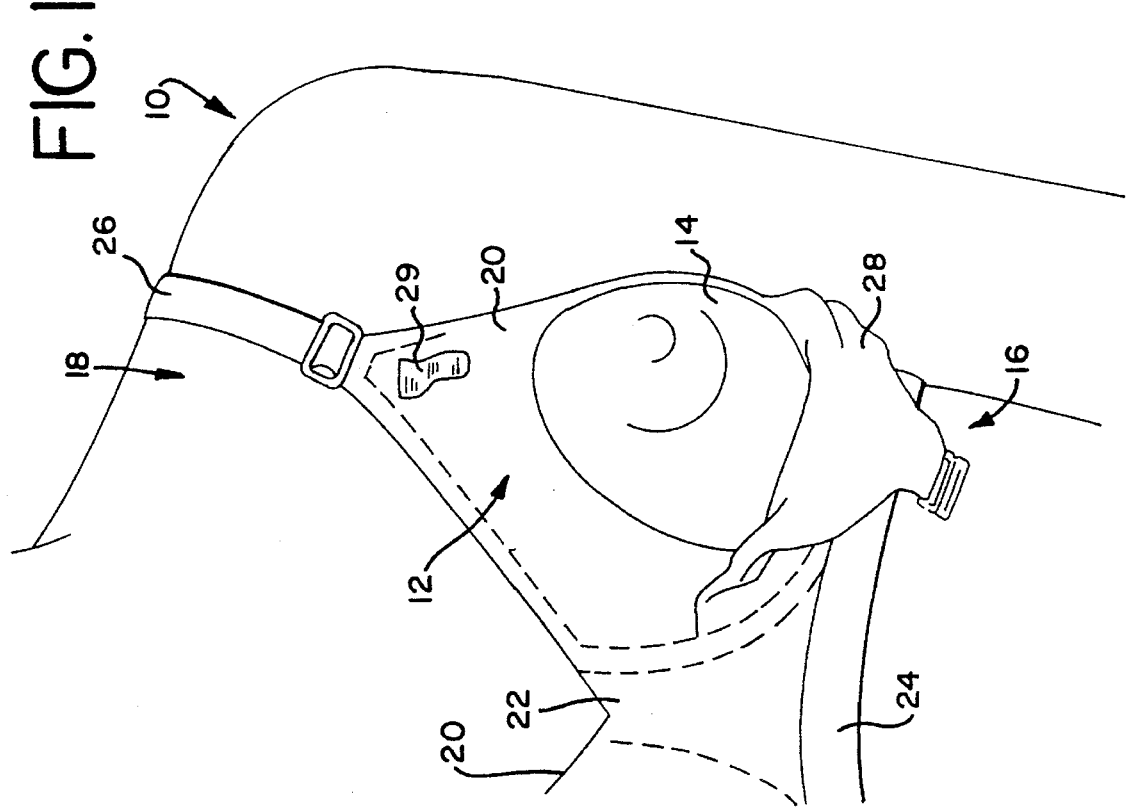

DEVICE AND KIT FOR SUPPORTING A BREAST SHIELD AND RELATED PUMP EQUIPMENT

This application is a continuation-in-part of U.S. patent application Ser. No. 08/375,977, now U.S. Pat. No. 5,514,166 filed Jan 20, 1995, which is incorporated by reference.

BACKGROUND OF THE INVENTION

This invention relates generally to breast pumps, and more particularly to a device for supporting a breast shield, as well as related breast pump equipment, on a woman's breast.

Breast pumps for expressing and storing breast milk for later use are well known. Two types of breast pumps are generally available for use by nursing mothers: motor-driver pumps and manually-operated pumps. Typically, these breast pumps include a funnel-shaped shield or hood that fits over the nipple and a substantial portion of the breast, some type of vacuum pump (e.g., manually driven piston cylinder, squeeze bulb or electrically driven vacuum device) which is connected to the breast shield for generating an intermittent vacuum in the breast shield, and a container for the expressed breast milk. The intermittent suction generated by the vacuum pump within the breast shield causes a pulling or pressing of the breast, and is intended to mimic an infant's suckling action to thereby express milk from the breast. The expressed milk typically flows from the breast shield to the collection container for storage and subsequent use by the infant. The collection container, such as a small milk bottle, is ordinarily assembled to the breast shield, as through an intermediate milk-directing channel and valve arrangement.

Brassieres, halter tops and other garments specifically designed for nursing mothers are also well known. Generally, these nursing brassieres include flaps which may be unfastened at one side from the brassiere to expose the breasts for nursing by an infant, or for enabling breast milk collection through pumping.

When desiring to use a breast pump to collect and store breast milk wearing such a nursing brassiere or otherwise, a mother, after exposing the breast, holds the breast shield in position on the exposed breast. Obviously, depending on whether the breast pump is motor-driven or manually-operated, and further on whether one or two breast shields are being used at the same time, one or both of the mother's hands will be needed to perform the breast pumping operation. As can be readily seen, the nursing mother, whether at home or at work, will not have the use of at least one of her hands, such as to perform other tasks when she is using her breast pump. Therefore, it would be advantageous to develop a method and device that will permit a mother to use a breast pump while also allowing her the free use of her hands to perform other tasks.

SUMMARY OF THE INVENTION

It is a principal objective of the present invention to provide a device that supports a breast shield of a breast pump upon an exposed breast in a "hands-free" manner for the user. The invention in its broadest sense contemplates any inanimate means whereby the breast shield is held in place on the breast without the need of the user or someone else to hold it in place. The breast shield support may be carried on the mother's body, or on a base which is movable to emplace the shield, or into which the mother can insert her breast(s). This is disclosed in co-pending patent application Ser. No. 08/375,977 filed on Jan. 20, 1995, which further discloses a number of embodiments of the invention.

The present application and invention is directed to yet another variant on the inventive concept. The embodiment of the present invention in one form has a mounting element which fits onto the back of a breast shield. The mounting element has posts thereon. Fabric loops are sewn into a brassiere. Bands, such as rubber bands, are knotted or otherwise attached to the fabric loops. The bands are then placed around the posts of the mounting elements in a manner that supports the breast pump in position against the breast, so that the mother does not have to use her hands to support the breast pump.

The foregoing embodiment preferably uses a slip-on, or snap-on, type mounting element which is contoured to the shape of the breast shield back (or rearward) portion. It can therefore be readily attached and detached. A plurality of posts are further advantageously provided to permit ease in adjusting and attaching the bands.

In an alternate form of the present invention, the posts of the mounting element can be formed integral with the breast shield.

The mounting element bands and/or the fabric loops can be provided in the form of a kit. A mother can thereby retrofit an existing nursing bra for use with the present breast pump assembly support.

These and other features and advantages of the present invention will be further understood upon consideration of the following detailed description of embodiments of the invention taken in conjunction with the drawings, in which:

BRIEF DESCRIPTION OF THE DRAWINGS

FIG. 1 is a perspective view of a brassiere in use showing the flap of the brassiere in an unfastened mode to expose the breast for nursing or breast pumping;

FIG. 2 is a perspective view of a representative breast pump assembly;

DETAILED DESCRIPTION OF PRESENTLY PREFERRED EMBODIMENTS

Figure 4:
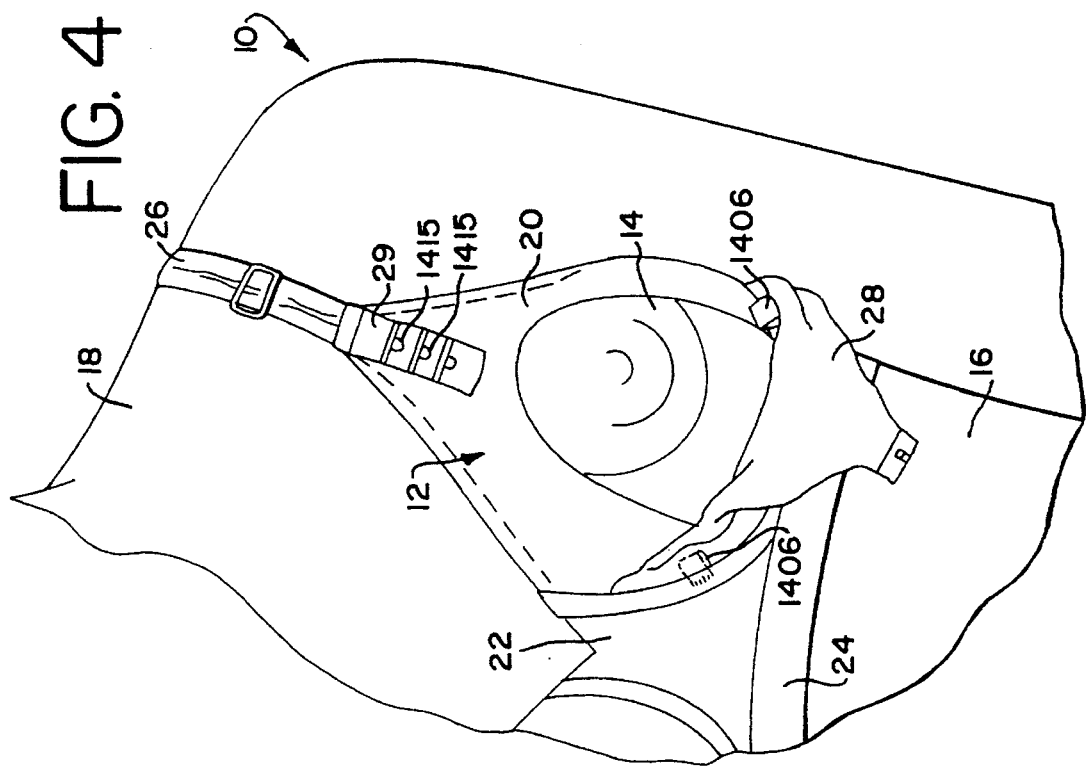
FIG. 4 is a perspective view of a brassiere showing loop placement used in an embodiment of the present invention.

For ease of illustration, the present invention is generally shown and described below in terms of a single breast pump used for expressing breast milk from a single breast. However, it is specifically contemplated that the present invention is usable to simultaneously support a breast shield on each of a woman's breasts for breast milk collection. In addition, like numerals will be used to designate like elements in the respective embodiments of the present invention.

Turning now to the drawings, FIG. 1 shows a partial view of a woman 10 wearing a brassiere 12. The brassiere 12 is adapted to conform around the breasts 14, torso 16 and shoulders 18 of the woman 10, to support the breasts 14. The brassiere 12 includes two breast cups 20 interconnected by a connecting band 22, a torso band 24 having two ends (not shown) which extend around and are connected at the woman's back, and shoulder straps 26 (one of which is not shown) which are disposed between the respective breast cups 20 and the ends of the torso band 24. To the foregoing extent, the brassiere 12 is conventional.

Even though the present invention is shown and described herein in terms of the brassiere 12 shown in FIG. 1, it is specifically contemplated that other types of brassieres, for example strapless brassieres, and other types of breast support garments, including halter tops, camisoles, and the like, may be used with the present invention, as will hereinafter be further understood.

As shown in FIG. 1, each of the breast cups 20 includes a flap 28 connected to the brassiere 12 near the bottom of the respective breast cup 20. The flap 28 is detachably connected to the brassiere 12 at a position near the respective shoulder straps 26 by a short strap 29. The flap 28 is oriented on the brassiere 12 such that it exposes the breast 14 for nursing or breast pumping as it is moved from the shoulder 18 to the torso 16. The flap 28 may be connected to the brassiere 12 in any suitable manner or orientation to expose the breasts 14.

A representative breast pump 30 for use with the present invention is shown in FIG. 2. The breast pump 30 includes a breast shield or hood 32 adapted to receive at least the nipple and some of the adjacent breast. The breast shield 32 receives the expressed breast milk, and directs the milk through a channel 34 to the milk collection container 36.

While the invention is for supporting the breast shield in place, in many if not most instances this will also require supporting the entirety of the breast pump (i.e. parts 32, 34 and 36 and related elements). Since the container 36 may carry on the order of 5 ounces of milk when full, the supporting device should be able to carry the weight of the pump and full container comfortably, and with the breast shield properly positioned throughout breast pumping.

A vacuum source 38 communicates with the breast shield 32 and the channel 34 through tubing 39, and creates the suction action in the breast shield 32 that expresses the breast milk from the breast 14. The vacuum source 38 comprises an electric motor-driven breast pump vacuum source for generating an intermittent vacuum. Furthermore, two breast shields 32 may be connected to the vacuum source for simultaneous "double-pumping" of both breasts 14. Other vacuum sources can of course be used with the present invention, such as a battery-driven pump, a manually operated hand-driven piston pump or a squeeze bulb type pump. The latter two are not considered to be particularly advantageous with the present invention, however, since one or both hands may be occupied with operating the manual pumps. For a more detailed description of motor-driven, battery-driven and manually-operated breast pumps, reference may be had to U.S. Pat. Nos. 4,857,051, 4,964,851 and 5,007,899.

Figure 3:
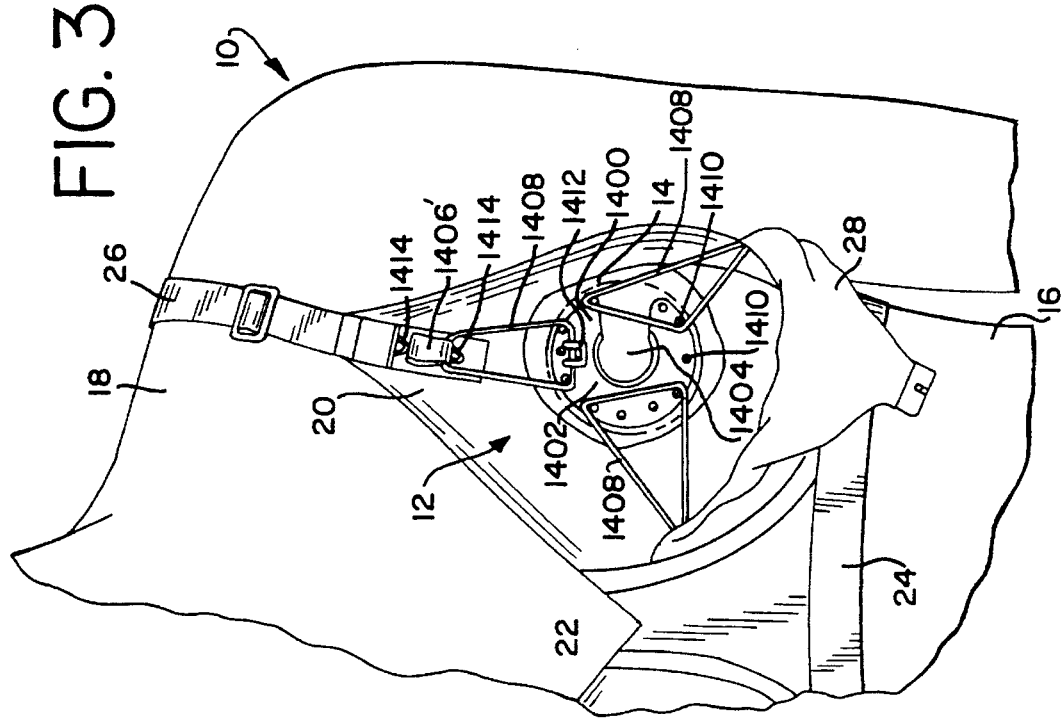
FIG. 3 is a perspective view of an embodiment of a breast shield support of the present invention, with the breast shield assembly removed for clarity.
Figure 6:
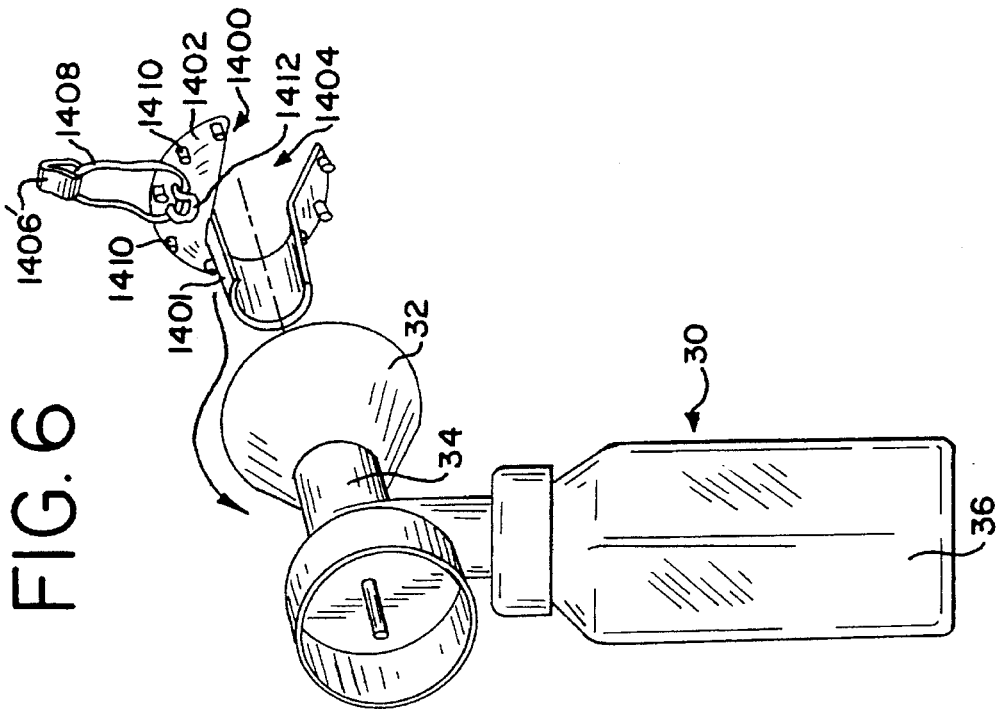
FIG. 6 is a perspective view of a mounting element made in accordance with the present invention and the breast pump.

FIG. 3 shows a first embodiment of the present invention of this application. The breast shield and assembly support includes a brassiere 12, a mounting element 1400 and attachments for the mounting element. As shown in FIG. 6, the mounting element 1400 is connected or attached to the breast shield 32 by fitting the mounting element 1400 snugly around the breast shield 32. This is accomplished in this embodiment with a tubular partial-cylinder portion 1401 of the mounting element which fits around the channel part 34 of the breast shield assembly in a slip-on or snap fit. The mounting element 1400 further has a shell portion 1402 which is contained to match that of the back of the breast shield 32. A cut-out 1404 accommodates the snap-fit for the mounting element over the cylindrical channel part 34. The mounting element is made of a rigid plastic, with sufficient flexibility to widen the split tubular portion 1401 to pass over and then embrace the breast pump cylinder portion 34. The mounting element 1400 is connected to the brassiere 12 and supported on the breast 14 by a plurality of loops and bands as will be more clearly shown hereafter.

Referring to FIG. 4, loops 1406 are connected to the breast cups 20 of the brassiere 12. The loops 1406 are made of fabric and sewn into the breast cups 20.

Figure 5:
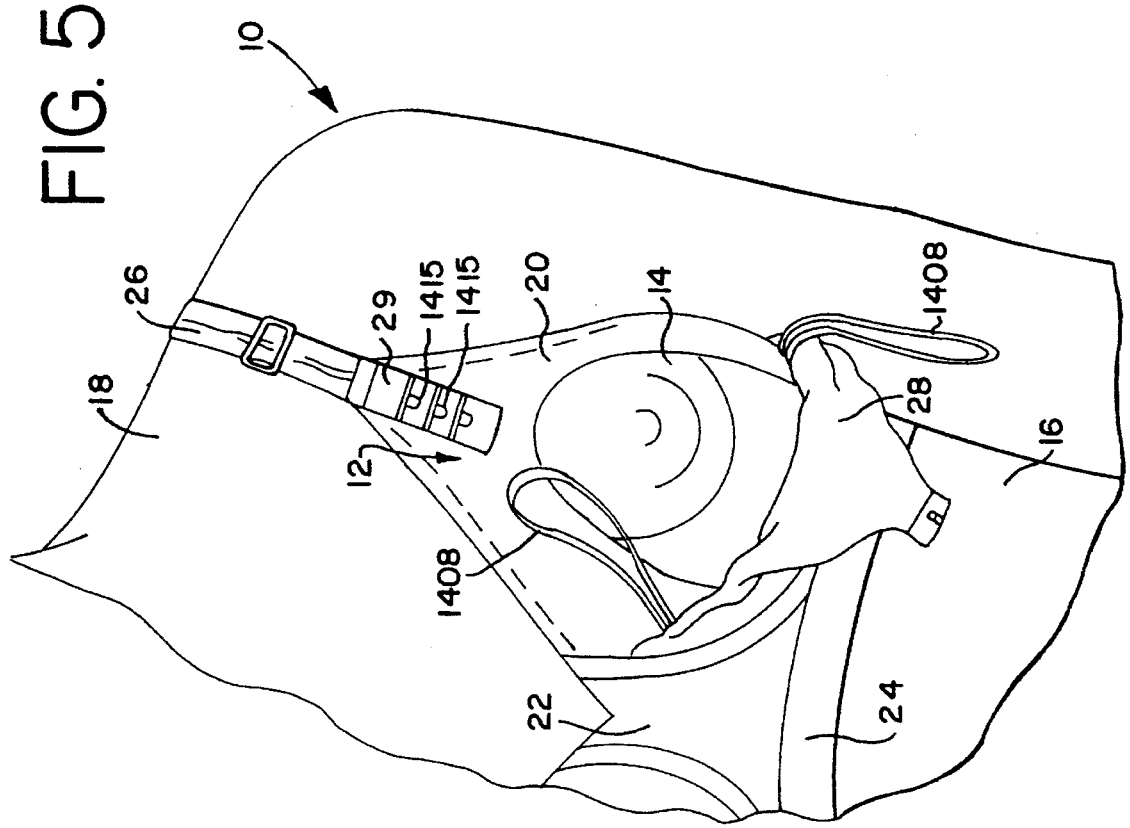
FIG. 5 is a perspective view of the brassiere of FIG. 4 showing placement of the bands.

Bands 1408 (FIG. 5) may be permanently attached to the loops 1406, or as presently preferred, the bands 1408 may be removably attached to the loops 1406. In the embodiment where the bands 1408 are removably attached to the loops 1406, a band 1408 is inserted through the loop 1406 and then the end of the band 1408 that has been inserted through the loop 1406 is then inserted through the opening of the other end of the band 1408, thereby removably tying the band 1408 to the loop 1406. The bands 1408 are of an elastic material, such as rubber bands.

Figure 7:
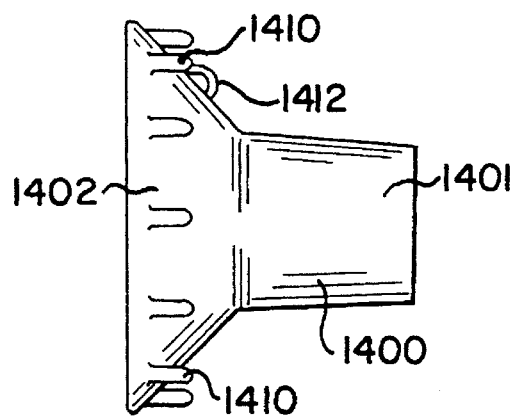
FIG. 7 is a side view of the mounting element of FIG. 6.
Figure 8:
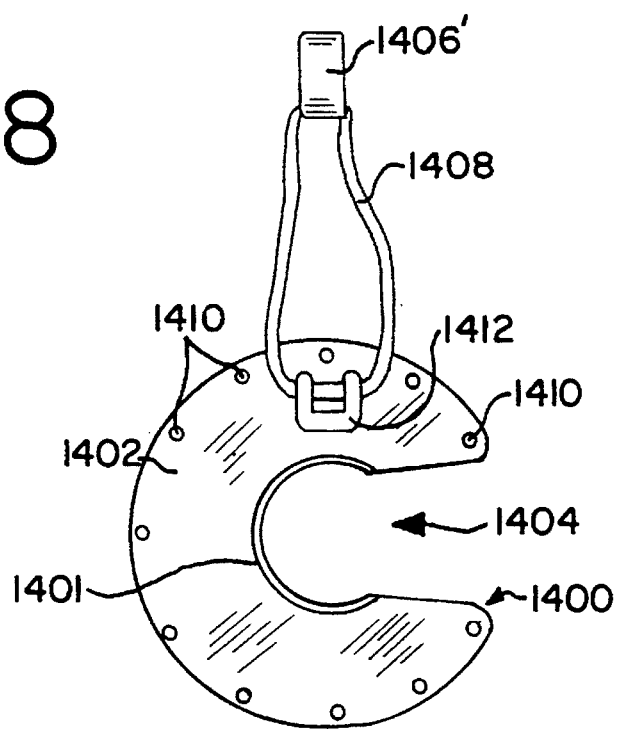
FIG. 8 is a front view of the mounting element of FIG. 7 with a band/loop attached.

As best shown in FIG. 7, the mounting element 1400 has a plurality of posts 1410, preferentially situated around the perimeter of the shell portion 1402 of the mounting element in regular spacing thereabout. The parts 1410 extend rearwardly relative to the shell portion 1402. With the mounting element in place (FIG. 3), the bands 1408 are placed around the posts 1410 in a manner that supports the breast pump 30 against the breast 14 so that the woman 10 does not have to use her hands to support the breast pump 30. The number of posts 1410 provided enables ready and various attachments of the bands 1408. The bands 1408 are anchored by the loops 1406.

In addition to the two points of attachments via the sewn loops 1406, the mounting element has a further attachment point via hook 1412.

Hook 1412 is provided to orient the mounting element 1400 and attached breast pump, with the hook 1412 being upward, i.e., above the breast. This provides a more sure point of attachment where the majority of the weight/torque will be applied, particularly as the bottle 36 fills during breast pumping. As seen in FIG. 3, posts 1410 may additionally be used in conjunction with the hook 1412 to secure the mounting element in place.

Figure 9:
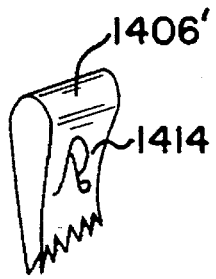
FIG. 9 is a perspective view of the loop of FIG. 8.

A fabric loop 1406' is associated with the band 1408 that is attached to the hook 1412. That loop 1406' may be removably attached to this band in the manner previously described. However, the loop 1406' that is to be secured to the shoulder strap 26 may be permanently attached to its band 1408, as shown in these Figures, as by sewing the loop together about the band. The loop 1406 is removably attached to the shoulder strap 26 using a hook fastener 1414, as shown in FIG. 9. The shoulder strap 26 has corresponding eye fasteners 1415. The hook fastener 1414 and the corresponding eye fasteners 1415 allow the fabric loop 1406' to thereby be removably and adjustably attached to the shoulder strap 26.

Figure 10:
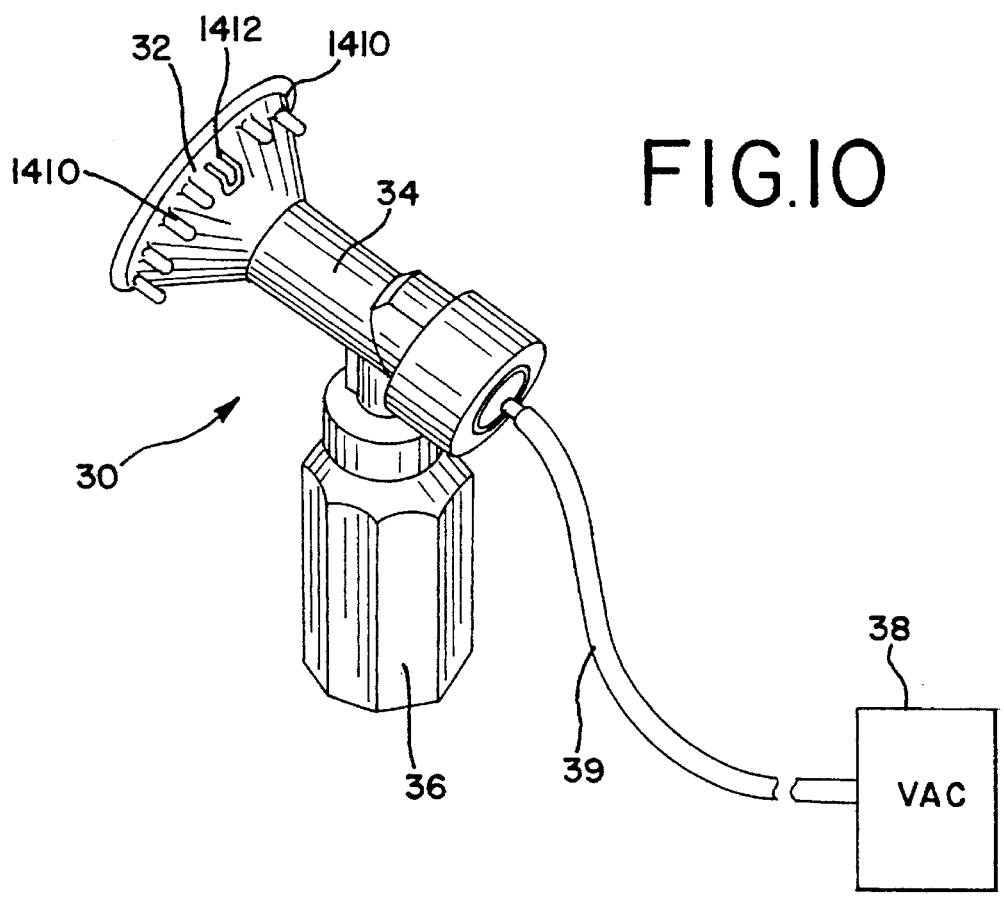
FIG. 10 is a modified embodiment where the mounting element is formed integral with the breast shield.
Figure 11:
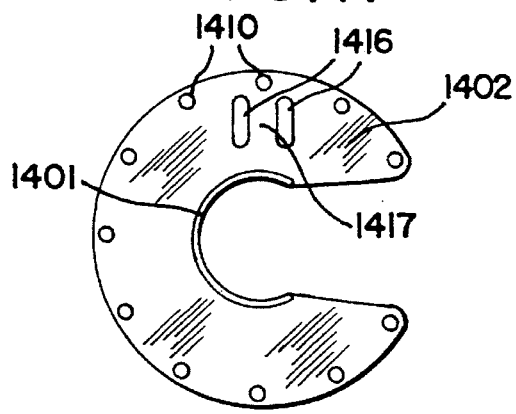
FIG. 11 is a modified mounting element similar to that of FIG. 8.

In another embodiment shown in FIG. 10, the mounting element may be eliminated by constructing the breast shield 32 with the posts 1410 and hook 1412 formed integral with breast shield 32. FIG. 11 shows a modified version of the mounting element 1400, where the hook 1412 has been replaced in function by a pair of parallel slots 1416, which define a rib 1417 therebetween. Band 1406' can be removably tied to the rib 1417 in the manner described with respect to the fabric loops. Rib 1417 is in essence a hook.

As stated above, the present invention permits a nursing mother to use a breast pump to collect and store breast milk, while also providing her with free use of her hands to perform other job tasks or chores. In addition, the present invention allows for hands-free "double pumping." Further, the present invention is simple to use and allows the breast shield to be quickly supported on the exposed breast.

It should be appreciated that the present invention may be modified or configured as appropriate for the application. The embodiments described above are to be considered in all respects only as illustrative and not restrictive. Changes may be made without departing from the spirit of the invention. The scope of the invention is indicated by the following claims rather than by the foregoing description. All changes which come within the literal meaning as well as the range of equivalency of the claims are to be embraced within their scope.

What is claimed is:

1. A breast pump assembly support device for holding a breast shield in place on a breast for expressing milk, comprising:

a garment to be worn around a woman's torso;

a pair of loops attached to said garment in opposed spaced relation;

a band attachable to each of said loops; and a mounting element having a plurality of posts extending from said breast shield to which said band is further attachable.

2. The breast pump support device of claim 1 wherein a band is removably attached to each of said loop.

3. The breast pump support device of claim 1 further including a third loop and another band attachable with said third loop, said third loop being releasably attachable to said garment by interengaged fasteners having elements thereof on each of said third loop and garment.

4. The breast pump support device of claim 3 wherein said band for said third loop is attachable by said another band to a hook formed on said mounting element.

5. The breast pump support device of claim 3 wherein said pair of loops are located in said garment such that they are on lower opposite sides of a breast received in said garment, and said third loop is attachable to said garment above the breast.

6. The breast pump support device of claim 1 wherein said mounting element is releasably attached to said breast pump assembly.

7. The breast pump support device of claim 6 wherein a rib is formed in said mounting element to which an additional band is attachable for connecting said additional band to a third loop, said third loop being releasably attachable to said garment of a point above a breast received in said garment.

8. A breast pump support device, wherein said breast pump includes a breast shield adapted to receive a breast therein for expressing milk, comprising:

a garment to be worn around a woman's torso, said garment including a pair of anchoring members formed in opposed relation within a part of the garment adapted to receive a breast therein;

a mounting element removably attached to said breast shield, said mounting element having a plurality of posts extending therefrom; and at least one band attachable to said anchoring element and said posts of said mounting element.

9. The breast pump support device of claim 8 wherein a plurality of elastic bands are respectively attached to an anchoring member.

10. The breast pump support device of claim 9 wherein said anchoring members are fabric loops to which said bands are respectively tied.

11. The breast pump support device of claim 9 wherein said mounting element includes a hook, with an additional loop being releasably attachable to a portion of said garment located above the breast in use, said releasable attachment being made by interengageable fastener elements provided on each of said garment and additional loop.

12. The breast pump support device of claim 11 wherein said additional loop is releasably attached to said garment via a hook and eye fastener.

13. The breast pump device of claim 10 wherein said mounting element, plurality of elastic bands and fabric loops are provided in a kit, said loops being sewn by a user in place within a garment.

14. The breast pump support device of claim 8 wherein said mounting element has a conical portion which is adapted to conform to a conical back of the breast shield, said conical portion having said posts formed thereon, and said mounting element has a split tubular portion which is adapted to fit around a cylindrical part of the breast pump.

15. The breast pump support device of claim 8 wherein said mounting element has a rib defined therein for connecting a band thereto, with an additional loop being provided and releasably attachable to said garment at a point located above a breast in use.

16. A device for supporting a breast shield of a breast pump assembly in place on a breast, comprising:

a garment having a breast-receiving portion adapted to receive a woman's breast therein;

a mounting element on said breast shield, said mounting element including a plurality of posts extending therefrom;

anchoring members on said garment on opposed sides of said breast-receiving portion; and at least one band attached to said anchoring members and said posts for fixing said breast shield within said garment against said breast.

17. The breast shield supporting device of claim 16 wherein said band is an elastic band which is stretched taut about said posts and against said anchoring members to fix said breast shield in place.

18. The breast shield supporting device of claim 16 wherein one of said anchoring members is a loop, and further including means for releasably fastening said loop to said garment at a point that is above a breast in said breast-receiving portion.

19. The breast shield supporting device of claim 16 wherein said anchoring members are a pair of fabric loops sewn in said breast receiving portion on lower and opposed sides thereof, and a third loop which has a fastener that is releasably attachable to said garment at a point that is above a breast in said breast-receiving portion, said mounting element further including a hook located in use of said mounting element at a point upward relative to the breast, and further including three elastic bands which are respectively attached to one of said loops, one of said bands furthermore connecting said third loop with said hook.

20. The breast shield supporting device of claim 16 wherein the breast shield has a conical shaped back part and a cylindrical part extending therefrom, said mounting element comprising a conical shell part which is adapted to conform to said back part of the breast shield, said shell part having a plurality of posts formed thereon along at least a portion of said shell part, and a tubular portion extending therefrom which is adapted to conform to said cylindrical part of the breast shield, said mounting element tubular portion being formed of a rigid but flexible material and split along a length for engagement of said tubular portion about said cylindrical part.

21. The breast shield supporting device of claim 16 wherein said mounting element is separate from said breast shield and includes means for releasably attaching said mounting element to the breast pump assembly.

22. A breast pump assembly which is supported in place on a breast, comprising:
   a garment having a breast-receiving portion adapted to receive a woman's breast therein;
   a plurality of posts extending from a breast shield which is adapted to overlie and receive a breast therein for expression of milk;
   anchoring members on said garment on opposed sides of said breast-receiving portion; and
   at least one band attached to said anchoring members and said posts for fixing said breast shield within said garment against said breast.

23. The breast pump assembly of claim 22 wherein said band is an elastic band which is stretched taut about said posts and against said anchoring members to fix said breast shield in place.

24. The breast pump assembly of claim 22 wherein one of said anchoring members is a loop, and further including means for releasably fastening said loop to said garment at a point that is above a breast in said breast-receiving portion.

25. The breast pump assembly of claim 22 wherein said anchoring members are a pair of fabric loops sewn in said breast receiving portion on lower and opposed sides thereof, and a third loop which has a fastener that is releasably attachable to said garment at a point that is above a breast in said breast-receiving portion, and further including three elastic bands which are respectively attached to an associated loop.

26. A kit for supporting a breast shield of a breast pump assembly in place on a breast, comprising:
   a plurality of anchoring members which are attachable to a garment on opposed sides of a portion of said garment adapted to receive a woman's breast therein;
   a mounting element including a plurality of posts extending therefrom and means for attaching said mounting element to said breast pump assembly; and
   at least one band which is attachable to said anchoring members and said posts for fixing said breast shield within said garment against said breast when said mounting element is attached to said breast pump assembly.

27. A kit for supporting a breast shield of a breast pump assembly in place on a breast, comprising:
   a plurality of loops which are attachable to a garment on opposed sides of a portion of said garment adapted to receive a woman's breast therein;
   a mounting element having a conical portion including a plurality of posts extending therefrom, said conical portion adapted to conform to a similarly conically-shaped back side of the breast shield, and an attachment part for releasably attaching said mounting element to the breast pump assembly;
   a plurality of elastic bands each of which is respectively attachable to a loop and about one or more of said posts for fixing the breast shield within said garment against said breast when said mounting element is attached to said breast pump assembly.

28. The kit of claim 27 wherein said loops are fabric loops which are to be sewn into the cup of a bra-type garment on opposite lower sides of the cup, one loop having part of a hook and eye fastener thereon which is attachable to the other part of said hook and eye fastener carried by said bra-like garment.

29. A device for supporting a breast shield of a breast pump assembly in place on a breast, comprising:
   a garment having a breast-receiving portion adapted to receive a woman's breast therein;
   a mounting element on said breast shield, said mounting element including a plurality of attachment parts thereon;
   anchoring members on said garment on opposed sides of said breast-receiving portion; and
   at least one band attached to said anchoring members and said attachment parts for fixing said breast shield within said garment against said breast.

30. The breast shield supporting device of claim 29 wherein said attachment parts comprise posts extending from said mounting element, said anchoring members comprise loops, and said at least one band comprises three elastic bands which are stretched taut about said posts and against a respective anchoring loop to which a respective band is attached to fix said breast shield in place.

31. A device for supporting a breast shield of a breast pump assembly in place on a breast, comprising:
   a bra-type garment having two breast-receiving cup portions each adapted to receive a woman's breast therein;
   a mounting element removably received on said breast pump assembly, said mounting element including a plurality of posts extending from around a conical portion of said mounting element which conical portion is adapted to conform to the back of a similarly conically-shaped breast shield, said conical portion having a cut-out segment adapted to pass over a cylindrical part of the breast pump assembly which extends from the breast shield, said mounting element further including a tubular portion which is split along its longitudinal length and adapted to embrace the cylindrical part of the breast pump assembly which is receivable therein;
   anchoring fabric loops sewn into said garment on opposed lower sides of each of said cups, and a free loop which is releasably attachable to said garment at a point above said cups;
   interengageable fastener elements on said free loop and said garment; and
   a plurality of elastic bands each attached to a respective loop and about one or more posts for fixing said breast shield within said garment against a breast when said bands are stretched taut about said posts and against a respective loop.

32. The device for supporting a breast shield of claim 30 wherein said mounting element further includes a hook formed thereon which hook is oriented generally above the breast when said mounting element is in place, a band attached to said free loop being attached to said hook.

* * * * *